(12) United States Patent
Shtarov et al.

(10) Patent No.: US 7,553,985 B2
(45) Date of Patent: Jun. 30, 2009

(54) FLUORINATED SURFACTANTS

(75) Inventors: Alexander Borisovich Shtarov, Wilmington, DE (US); Michael Joseph Michalczyk, Wilmington, DE (US); Charles Kenneth Taylor, Thorofare, NJ (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 551 days.

(21) Appl. No.: 11/265,037

(22) Filed: Nov. 2, 2005

(65) Prior Publication Data

US 2007/0099018 A1    May 3, 2007

(51) Int. Cl.
C07F 9/02    (2006.01)

(52) U.S. Cl. ..................................................... 558/204

(58) Field of Classification Search ................... None
See application file for complete search history.

(56) References Cited

U.S. PATENT DOCUMENTS

| | | | |
|---|---|---|---|
| 3,016,406 A | 1/1962 | Brace | |
| 3,145,222 A | 8/1964 | Brace | |
| 3,171,861 A | 3/1965 | Ahlbrecht | |
| 3,172,910 A | 3/1965 | Brace | |
| 3,239,557 A | 3/1966 | Fasick | |
| 3,514,487 A | 5/1970 | Anello et al. | |
| 3,721,706 A | 3/1973 | Hoffmann et al. | |
| 3,773,826 A | 11/1973 | Rondestvedt, Jr. | |
| 3,781,370 A | 12/1973 | Anello et al. | |
| 3,786,089 A | 1/1974 | Rondestvedt, Jr. | |
| 3,825,577 A | 7/1974 | Lalu et al. | |
| 3,836,577 A | 9/1974 | Jaeger et al. | |
| 4,490,304 A | 12/1984 | Falk | |
| 4,983,769 A | 1/1991 | Bertocchio et al. | |
| 5,302,212 A | 4/1994 | Desbiendras et al. | |
| 5,639,923 A | 6/1997 | Von Werner | |
| 5,908,966 A | 6/1999 | Krespan et al. | |
| 6,379,394 B1 | 4/2002 | Chilou et al. | |
| 6,664,354 B2 | 12/2003 | Savu et al. | |

FOREIGN PATENT DOCUMENTS

| | | |
|---|---|---|
| DE | 1942264 A | 2/1970 |
| DE | 2140261 | 2/1973 |
| DE | 3016571 | 11/1981 |
| DE | 3035641 | 5/1982 |
| EP | 0340753 A2 * | 5/1989 |
| EP | 1 195 370 A1 | 4/2002 |
| ES | 2207420 | 5/2004 |
| FR | 1600425 A | 7/1970 |
| GB | 904261 | 8/1962 |
| JP | 57197234 | 12/1982 |
| WO | WO 95/11877 | 5/1995 |
| WO | WO 2004/041757 A1 | 5/2004 |

OTHER PUBLICATIONS

Brace et al.; Effect of a Perfluoroalkyl Group on the Elimination and Substitution Reactions of Two Homologous Series of Perfluoroalkyl-Substituted Iodoalkanes; Journal of Organic Chemistry 1984, 49(13), 2361-2368; American Chemical Society.

Abstract—Guyot et al.; Kinetics of homopolymerization of fluorinated acrylates. Part 5. Influence of the spacer between the fluorinated chain and the ester group; Macromolecular Chemistry and Physics (1998), 199(9), 1879-1885; Huethig & Wepf Verlag.

Abstract—Steytler et al.; Phosphate Surfactants for Water-in-CO2 Microemulsions; Langmuir (2001), 17(25), 7948-7950; American Chemical Society.

Pees et al.; Synthesis and physiocochemical characterization of—perfluorooctyol-alkyl polyacrylates: odd-even effect; European Polymer Journal (2002), 38(5), 921-931; Elsevier Science Ltd.

Guo et al.; New Non-Biopersistant Fluorinated Alkyl Methacrylate Polymers; University of North Carolina at Chapel Hill, FluoroScienence LLD, North Carolina State University.

* cited by examiner

Primary Examiner—Paul A Zucker
(74) Attorney, Agent, or Firm—Nancy S. Mayer

(57) ABSTRACT

A composition of formula I

[Rf(CH2)m(O)n]x-A wherein
$R_f$ is a straight or branched perfluoroalkyl group having from about 2 to about 20 carbon atoms, or a mixture thereof,
m is a positive integer equal to or greater than 3,
n is 0 or 1,
x is 1 to about 3,
A is $-P(O)(OR^1)_y(OM^+)_{3-y-x}$, $-C(O)CH(SO_3^-M^+)CH_2C(O)-$, $-(CH_2CH_2O)_d(CH_2CHR^2O)_eR^3$, or $-SO_2B$,
$M^+$ is an alkali metal ion, $NH_4^+$, or $NH_2^+(CH_2CH_2OH)_2$,
B is $N(R^2)_2$ or $N(CH_2CH_3)(CH_2CH_2OH)$,
$R^1$ is $C_1$ to $C_3$ alkyl,
$R^2$ is $C_1$ to $C_4$ alkyl,
$R^3$ is H or $CH^3$,
y is 0 to about 1,
d is 0 to about 16,
e is 0 to about 16, provided that (d+e) is from about 3 to about 16 is disclosed.

8 Claims, No Drawings

FLUORINATED SURFACTANTS

BACKGROUND OF THE INVENTION

Perfluoroalkylethyl iodides, $C_kF_{(2k+1)}CH_2CH_2I$, termed "Telomer B iodides", are prepared by insertion of an ethylene molecule into the perfluoroalkyl iodides of the structure $C_kF_{(2k+1)}I$, "termed Telomer A iodides". Perfluoroalkylethyl iodides are starting materials for the preparation of fluorinated surfactants and treatment chemicals to provide surfaces with hydrophobic and oleophobic properties. Compounds made from such iodides include, for example, perfluoroalkylethyl(meth)acrylates and various other compounds containing the perfluoroalkylethyl group, and find commercial use in the modification of surface properties. See, for example U.S. Pat. No. 3,721,706.

For surfactants and surface treatment agents containing perfluoroalkyl chains, longer perfluoroalkyl chains contain a higher percentage of fluorine at a given concentration and generally provide better performance. However, fluorinated materials are more expensive. Reducing the fluorine content would reduce the cost, but it is necessary to maintain product performance. Reduction of the fluorine content with delivery of the same or higher performance is therefore desirable.

It is desirable to improve surfactant or surface treating agent performance and to increase the fluorine efficiency, i.e., boost the efficiency or performance of the surfactants or treating agents so a lower proportion of the expensive fluorine component is required to achieve the same level of performance, or to have better performance using the same level of fluorine. It is also desirable to have an economical pathway for preparation of such fluorine efficient surfactants and surface treating agents from perfluoroalkyliodides.

Two methods for the preparation of perfluoroalkylethyl (meth)acrylates from perfluoroalkylethyliodides are:
(1) reaction of the perfluoroalkylethyl iodide with a (meth) acrylic acid salt such as potassium (meth)acrylate, as described by Fasick et al. in U.S. Pat. No. 3,239,557; and
(2) reaction of the perfluoroalkylethyl iodide with oleum and further hydrolysis of the sulfates with water in sulfuric acid to yield perfluoroalkylethanol, as described by Day in U.S. Pat. No. 3,283,012, followed by esterification with (meth) acrylic acid or transesterification with an alkyl (meth)acrylate.

The first process is accomplished in a single step but yields are lowered by the formation of byproduct perfluoroalkylethylene. The second process involves two reaction steps, the use of oleum, but is free of byproduct perfluoroalkylethylene.

There is a need for surfactants and surface treating agents providing equivalent or improved performance while reducing the proportion of fluorine required due to its expense, and for economical pathways to such products. The present invention provides such surfactants having higher fluorine efficiency and an improved method to obtain perfluoroalkyl-containing monomers.

SUMMARY OF THE INVENTION

The present invention comprises a composition of Formula I

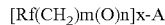

wherein $R_f$ is a straight or branched perfluoroalkyl group having from about 2 to about 20 carbon atoms, or a mixture thereof,
m is a positive integer equal to or greater than 3,
n is 0 or 1,
x is 1 to about 3,
A is $-P(O)(OR^1)_y(OM^+)_{3-y-x}$, $-C(O)CH(SO_3^-M^+)$ $CH_2C(O)-$, $-(CH_2CH_2O)_d(CH_2CHR^2O)_eR^3$, or $-SO_2B$,
$M^+$ is an alkali metal ion, $NH_4^+$, or $NH_2^+(CH_2CH_2OH)_2$,
B is $N(R^2)_2$ or $N(CH_2CH_3)(CH_2CH_2OH)$,
$R^1$ is $C_1$ to $C_3$ alkyl,
$R^2$ is $C_1$ to $C_4$ alkyl,
$R^3$ is H or $CH_3$,
y is 0 to about 1,
d is 0 to about 16,
e is 0 to about 16, provided that (d+e) is from about 3 to about 16.

The present invention further comprises a method of lowering the tension at the surface of contact between two phases comprising contacting said surface with a composition of Formula I as defined above.

The present invention further comprises an improved process for the preparation of perfluoroalkylalkyl acrylate or perfluoroalkylalkyl methacrylate by reaction of a) sodium acrylate or potassium acrylate, or b) sodium methacrylate or potassium methacrylate, respectively, with perfluoroalkylalkyliodide wherein the improvement comprises use of a long chain iodide of formula $R_f(CH_2)_mI$ wherein $R_f$ is a straight or branched perfluoroalkyl group having from about 2 to about 20 carbon atoms, or a mixture thereof, which is optionally interrupted by at least one oxygen atom, and m is a positive integer equal to or greater than 3.

DETAILED DESCRIPTION

Herein tradenames are shown in upper case.

The term "(meth)acrylate" as used herein includes both acrylate and methacrylate.

The present invention comprises surface-active compositions or surfactants of formula $$[R_f(CH_2)_m(O)_n]_x\text{-A} \qquad \text{Formula 1}$$

wherein $R_f$ is a straight or branched chain perfluoroalkyl group having 2 to about 20 carbon atoms, or a mixture thereof;
m is a positive integer greater than or equal to 3;
n is 0 or 1;
x is 1 to about 3 and is determined by the valence of A;
A is $-P(O)(OR^1)_y(OM^+)_{3-y-x}$, $-C(O)CH(SO_3^-M^+)$ $CH_2C(O)-$, $-(CH_2CH_2O)_d(CH_2CHR^2O)_eR^3$, or $-SO_2B$,
wherein
$M^+$ is an alkali metal ion, $NH_4^+$, or $NH_2^+(CH_2CH_2OH)_2$,
$R^1$ is $C_1$ to $C_3$ alkyl, and
$R^2$ is $C_1$ to $C_4$ alkyl,
$R^3$ is H or $CH_3$,
B is $-N(R^2)_2$ or $N(CH_2CH_3)(CH_2CH_2OH)$,
y is 0 to about 1,
d is 0 to about 16,
e is 0 to about 16, provided that (d+e) is from about 3 to about 16.

The iodides of the structure $R_f(CH_2)_mI$ wherein $R_f$ and m are defined as above are precursors used in the preparation of the compositions of the present invention. These iodides are prepared by reacting $R_fI$ with ethylene under pressure at elevated temperatures and optionally in the presence of a free radical source as described by Brace in U.S. Pat. No. 3,145,222. The alcohols of the structure $R_f(CH_2)_mOH$ wherein $R_f$ and m are as defined above are prepared by contacting the iodide $R_f(CH_2)_mI$ with N,N-dimethylformamide or 1-methyl-2-pyrolidinone and water at an elevated temperature (about 120° C.).

Phosphate surfactants of the present invention are of Formula I wherein A is —$P(O)(OR^1)_y(O^-M^+)_{(3-y-x)}$, and x is 1 to about 2. $R^1$ is preferably iso-propyl. The phosphate surfactants of the present invention also can contain phosphate byproducts such as mixed pyrophosphates of formula [$R_f$—$(CH_2)_mO]_xP(O)(OR^1)_y$—O—$P(O)[R_f(CH_2)_mO]_x(OR^1)_y$ wherein $R_f$, $R^1$, m, x and y are as defined above for Formula I, and non-fluorinated phosphates, such as $R^1O$—$(NH_4O)_2P(O)$ wherein $R^1$ is as defined above for Formula I, due to the reaction of the $R^1OH$ alcohol. Such byproducts have no significant effect on the surfactant properties of the compositions of the present invention. The phosphate surfactants of the present invention are prepared by reacting the alcohol $R_f(CH_2)_mOH$ with phosphorus pentoxide. This is followed by the addition of $R^1OH$, preferably isopropanol, to ensure a complete reaction. It is then neutralized with aqueous ammonia or other water-soluble amines such as $NH(CH_2CH_2OH)_2$. These phosphate surfactants even with a short perfluoroalkyl chain (such as when $R_f$ is perfluorobutyl and m is equal to 3 or 4), when dissolved in water provide a greater decrease in surface tension than the corresponding surfactants with m equal to 2 on an equal weight, fluorine percent, or equimolar concentration basis. Additionally they result in a more efficient use of the fluorine moiety; that is, a greater surface tension decrease is obtained with less fluorine, providing an economic advantage.

The polyalkylene oxide surfactants of the present invention are of Formula I wherein A is —$(CH_2CH_2O)_d(OCH_2CHR^2O)_eOR^3$. The polyalkylene oxide surfactants are prepared by contacting $R_f(CH_2)_mOH$ with sodium borohydride and ethylene oxide.

The sulfosuccinate surfactants of the present invention are of Formula I wherein A is the divalent group —$C(O)CH(SO_3^-M^+)CH_2C(O)$— and x is 2. These surfactants are prepared by reacting $R_f(CH_2)_mOH$ with maleic anhydride and treating the maleate diester with sodium bisulfite to yield $R_f(CH_2)_mOC(O)CH(SO_3^-M^+)CH_2C(O)O(CH_2)_mR_f$.

The surfactants of Formula I wherein A is $SO_2B$ are prepared by reaction with a sulfonyl halide of the structure $R_f(CH_2)_mS(O_2)X$, and wherein X is a halogen. These are prepared by reacting $R_f(CH_2)_mI$ wherein $R_f$ and m are defined as above in Formula I with potassium thiocyanate, followed by oxidation with halogen, preferably chlorine, in the presence of water (e.g., as in U.S. Pat. No. 3,825,577). When B is $N(R^2)_2$, the sulfonyl halide is reacted with $H_2NR^2$ $NH(R^2)_2$ wherein $R^2$ is independently $C_1$ to $C_4$ alkyl, typically in an ether solvent. When B is —$N(CH_2CH_3)(CH_2CH_2OH)$, the sulfonyl halide is reacted first with $H_2NC_2H_5$ and then with ethylene oxide.

These anionic and non-ionic surfactant compositions of Formula I are useful as a general surfactants at loadings much lower than the corresponding compositions wherein m is 2. They are also useful as leveling agents for various surfaces.

The compositions of claim 1 can further comprise a surface treatment agent. Suitable surface treatment agents include those which provide a surface effect with or without ironing which is shrinkage control, wrinkle free, permanent press, moisture control, softness, strength, anti-slip, antistatic, anti-snag, anti-pill, stain repellency, stain release, soil repellency, soil release, water repellency, oil repellency, odor control, antimicrobial, or sun protection.

The present invention further comprises a method of lowering the tension at the surface of contact between two phases comprising contacting said surface with a composition of Formula I $$[R_f(CH_2)_m(O)_n]_x\text{-A}$$

wherein $R_f$ is a straight or branched perfluoroalkyl group having from about 2 to about 20 carbon atoms, or a mixture thereof,
m is a positive integer equal to or greater than 3,
n is 0 or 1,
x is 1 to about 3, and
A is —$P(O)(OR^1)_y(OM^+)_{3-y-x}$, —$C(O)CH(SO_3^-M^+)CH_2C(O)$—, —$(CH_2CH_2O)_d(CH_2CHR^2O)_eR^3$, or —$SO_2B$,
$M^+$ is an alkali metal ion, $NH_4^+$, or $NH_2^+(CH_2CH_2OH)_2$,
B is $N(R^2)_2$ or $N(CH_2CH_3)(CH_2CH_2OH)$,
$R^1$ is $C_1$ to $C_3$ alkyl, and
$R^2$ is $C_1$ to $C_4$ alkyl,
$R^3$ is H or $CH_3$,
y is 0 to about 1,
d is 0 to about 16,
e is 0 to about 16, provided that (d+e) is from about 3 to about 16.

The contacting of the surfactant composition with the surface is by coating, brushing, painting, spraying, or other suitable means. The two phases are each independently a solid or a liquid, and include fibrous surfaces or hard surfaces. Typically the surfactant is applied as a liquid, emulsion, or solution to a fibrous or hard surface. Fibrous surfaces include fibers, yarns, fabrics, textiles, carpets, and the like. Hard surfaces include porous and non-porous mineral surfaces such as glass, stone, masonry, concrete, tile, brick, clay, wood, granite, marble, limestone, mortar, gypsum, terrazzo, and composite materials. The composition of the present invention is especially useful when applied as a coating on a surface.

In another embodiment, the present invention comprises a process for the preparation of perfluoroalkylalkyl (meth)acrylates by reaction of a (meth)acrylate salt with a perfluoroalkylalkyl iodide of the structure $R_f(CH_2)_mI$, wherein $R_f$ is a straight or branched perfluoroalkyl group having from about 2 to about 20 carbon atoms, or a mixture thereof, which is optionally interrupted by at least one oxygen atom, and m is a positive integer equal to or greater than 3. The reaction is preferably conducted in an anhydrous monohydric secondary or tertiary alcohol solvent, most preferably t-butanol, at a reaction temperature of from about 125° C. to about 200° C. Unexpectedly, the reaction yield when m is greater than or equal to 3 is about 95% and is not diminished by the formation of byproduct ethylenic compounds as occurs in the reaction wherein m is 2. The corresponding molar yield when m is 2 is about 80-85%. The (meth)acrylate salt used in this process is an alkali metal salt and is preferably potassium or sodium (meth)acrylate. The reaction to produce the perfluoroalkylalkyl (meth)acrylate is:

$$R_f(CH_2)_mI + MOC(O)CR^3=CH_2 \rightarrow R_f(CH_2)_mOC(O)CR^3=CH_2 + MI$$

wherein $R_f$ and m are as defined above, $R^3$ is H or $CH_3$, and M is an alkali metal salt. The improved process of the present invention is useful to prepare perfluoroalkylalkyl acrylates and perfluoroalkylalkyl (meth)acrylates wherein m is greater than or equal to 3. The formed perfluoroalkylalkyl acrylates and perfluoroalkylalkyl (meth)acrylates are further recovered from the reaction mixture, preferably by filtration and distillation methods. The present invention further comprises products prepared by this improved process. These products prepared by the process of the present invention are useful as monomers in emulsion or solution co-polymerization with (meth)acrylates, vinyl chloride, vinylidene chloride and other olefins to prepare useful polymers and copolymers. These polymers and copolymers wherein m is greater than or equal to 3 provide soil resistance, stain resistance, oil repellency and water repellency to fibrous and hard substrates as defined above.

The surfactant compositions of the present invention, and the perfluoroalkylalkyl (meth)acrylates prepared by the process of the present invention have increased fluorine efficiency compared to analogous prior art compositions wherein m is 2. By increasing m, the hydrocarbon portion of the composition is increased relative to the fluorine portion, yet the surface effect performance is the same or better.

Materials and Test Methods

VAZO-67 is 2.2'-azobis(2-methylbutyronitrile) and is available from E. I. du Pont de Nemours and Company, Wilmington Del.

Perfluoroalkyl iodides used as reactants in the Examples were prepared as follows. Perfluorohexyl iodide (67 g, 150 mmol) and VAZO-67 (0.45 g, 1.6 mol. %) were charged to a 450 mL shaker tube and purged with nitrogen. The tube was charged with ethylene and heated to 80° C. for 4 hours with 1200 psig ($8.27 \times 10^6$ Pa) of ethylene. By GC/FID analysis, the product of the reaction contained $C_6F_{13}CH_2CH_2I$ (2.4%), $C_6F_{13}(CH_2)_4I$ (76.9%), $C_6F_{13}(CH_2)_6I$ (14.7%), $C_6F_{13}(CH_2)_8I$ (5.3%). Other homologs of the perfluoroalkylalkyl iodides were prepared using the same process using the corresponding starting $R_fI$ iodides. The products can be further used as a mixture of homologs or distilled in vacuum to obtain more narrow homolog distributions and individual homologs.

Perfluoroalkyl alcohols used as reactants in the Examples were prepared as follows. $C_6F_{13}$—$(CH_2)_m$—I (6.0 g), m=2 (6.8%), 4 (55.85%), 6 (24.85%), 8 (7.55%) with average MW=512) was charged into the round bottom flask and reacted with N,N-dimethylformamide (20 molar equivalents) and water (8 molar equivalents) at 120° C. for 15 h to obtain complete conversion into the $C_6F_{13}$—$(CH_2)_m$—OH (with less than 1% of olefin elimination products by GC/FID). The reaction mixture was further washed three times with water, and product dried in vacuum to remove the residual water and N,N-dimethylformamide. The products can be further used as a mixture of homologs or distilled in vacuum to obtain more narrow homolog distributions and individual homologs. Other homologs of the perfluoroalkyl alcohols were prepared using the same process using the analogous starting materials.

Test Method 1—Measurement of Surface Tension.

The surface tension measurements of anionic surfactants were measured in deionized water by the use of Wilhelmy plate (Kraus USA, Nazareth, Pa.) method on an automated Kruss tensiometer used in accordance with the manufacturers' manuals. Lower surface tension values at a given concentration denote improved surfactant properties.

EXAMPLES

Example 1

To a round-bottom flask fitted with a mechanical stirrer and sparged with nitrogen was added $C_4F_9(CH_2)_4OH$ (40.1 g). While stirring at 23-24° C., phosphorus pentoxide (8.8 g) was added in portions over a period of 5.5 h. The reaction mixture was then heated to 95° C. for 17 h. After heating, isopropanol (37.8 g) was added over a period of 2 h while the mixture cooled from 95° C. to 65° C. Aqueous ammonia solution (15.9 g, 27%) was then added to the reaction mixture; the temperature rose from 65 to 68° C. during the addition. Deionized water was added next, and the mixture was stirred at 60° C. for 2 h and cooled to room temperature yielding an aqueous solution of the anionic surfactant. The surface tension of the surfactant was measured in deionized water using Test Method 1. Results are listed in Table 2.

Examples 2 and 3

The procedure of Example 1 was repeated replacing the $C_4F_9(CH_2)_4OH$ with an equimolar amount of the perfluoroalkylalkanols $C_4F_9(CH_2)_3OH$ (Example 2), or $C_6F_{13}(CH_2)_4OH$ (Example 3) alcohols to produce the corresponding phosphate surfactants. The surface tension was measured in deionized water using Test Method 1. Results are in Table 2.

Comparative Example A

The procedure of Example 1 was repeated replacing the $C_4F_9(CH_2)_4OH$ with an equimolar amount of the perfluorobutylethanol $C_4F_9CH_2CH_2OH$ to produce the corresponding phosphate surfactant as a control example.

$^{31}P$ NMR was used to determine the mole % of the various phosphates in the above Examples as shown in Table 1.

TABLE 1

| Phosphate formula, where $R_f = C_kF_{(2k+1)}$— | Example 1 k = 4, m = 4 | Example 2 k = 4, m = 3 | Example 3 k = 6, m = 4 |
|---|---|---|---|
| $R_f$—$(CH_2)_m$O—$(NH_4O)_2P(O)$ | 38.3 | 34.6 | 23.4 |
| $(R_f$—$(CH_2)_mO)_2$—$(NH_4O)P(O)$ | 31.2 | 40.6 | 36.4 |
| $(R_f$—$(CH_2)_mO)$ | 8.0 | — | 2.5 |
| $(CH_3)_2CHO$—$(NH_4O)P(O)$ | | | |
| $(R_f$—$(CH_2)_mO)_3P(O)$ | 4.6 | — | — |
| $(CH_3)_2CHO$—$(NH_4O)_2P(O)*$ | 11.8 | 2.2 | 6.0 |
| Pyrophosphates* (total) | 6.0 | 22.4 | 31.6 |

*byproducts.

TABLE 2

| | Surface tension* | | | |
|---|---|---|---|---|
| Conc. (wt %) | k = 4, m = 2 Comp. Ex. A (Control) | K = 4, m = 3 Ex. 1 | k = 4, m = 4 Ex. 2 | k = 6, m = 4 Ex. 3 |
| 0.0001 | — | 67.22 | 52.31 | 67.94 |
| 0.0005 | 76.46 | 44.29 | 49.00 | 38.89 |
| 0.001 | 46.61 | 37.12 | 46.82 | 36.51 |
| 0.005 | 42.52 | 29.46 | 38.05 | 20.49 |
| 0.01 | 38.76 | 27.06 | 33.13 | 19.77 |
| 0.05 | 32.91 | 18.95 | 24.13 | 17.10 |
| 0.1 | 25.94 | 16.62 | 19.48 | 16.76 |
| 0.2 | 19.26 | 16.61 | 15.37 | 16.73 |
| 0.5 | 16.47 | 16.38 | 15.34 | 15.30 |
| 1 | — | 16.25 | 15.49 | 14.56 |

*dyne/cm, ($\times 10^{-7}$ = N/m)

Table 2 shows that, at weight % concentrations of 0.0001% to 0.5%, the surface tension was lower (greater surfactant effect) for the surfactants of the present invention (m greater than 2) than for the corresponding surfactant having the same amount of fluorine (k=4) with m equal to 2.

Example 4

Perfluoroalkylalkyl alcohol and sodium borohydride (5 mol. %) is charged into a round bottom flask equipped with mechanical stirring and a cold finger condenser (at about −70° C.) and reacted at 85 to 130° C. under nitrogen. The temperature is adjusted to 65 to 100° C., when ethylene oxide is fed over time to the reaction flask, maintaining conditions to avoid the formation of potentially explosive air-ethylene oxide mixtures and uncontrolled reaction of ethylene oxide with solid sodium borohydride. The reaction with ethylene oxide is continued at 65 to 100° C. until the required equivalents of ethylene oxide (typically about 5 to 10 equivalents) are consumed. Vacuum is applied to remove the residual ethylene oxide, and flask is refilled with nitrogen. The product perfluoroalkylalkyl polyethyleneglycol $C_kF_{(2k+1)}$—$(CH_2)_m$—$O(CH_2CH_2O)_d$—H is diluted with water and optionally other co-solvent for further use and surface tension measurements.

Example 5

Anhydrous potassium carbonate (0.66 g) was placed into 20 mL vial containing 10 mL of dimethylformamide and stirred at 70° C. for 1 h. Then $C_4F_9$—$(CH_2)_m$—I (0.84 g), m=2 (4.0%), m=4 (78.3%), m=6 (14.3%), m=8 (1.58%) average MW=406) was added and the solution was stirred for additional 40 min at 70° C. Polyethylene glycol monomethyl ether (1.0 g, average MW=350) was added and the reaction mixture stirred at 70° C. for 20 h. GC/MS and GC/FID analysis showed greater than 98% conversion of $C_4F_9$—$(CH_2)_m$—I with formation of by-product perfluoroalkylalkyl-ethylenes $C_4F_9$—$(CH_2)_{m-2}$—CH=CH2 (36-64%). The reaction mixture was cooled to room temperature and 30 mL of deionized water was added. The product $C_4F_9$—$(CH_2)_mO(CH_2CH_2O)_d$—$CH_3$, wherein m was as defined above for the starting iodide and d was an average of 7.2, was extracted from this solution using diethyl ether. The organic layer was washed with deionized water and dried with $MgSO_4$. Solvent was removed under reduced pressure and the crude product was dried in a vacuum oven at 1 mmHg (133 Pa) at 90° C. to obtain 0.35 g (23%) of yellow solid.

Example 6

1H,1H,2H,2H,3H,3H,4H,4H-nonafluorooctanol $C_4F_9CH_2CH_2CH_2CH_2OH$, prepared using the method as described above under Materials, (58 g, 0.2 mol), maleic anhydride (9.8 g, 0.1 mol), p-toluene sulfonic acid monohydrate (2 g, 10 mmol) and 150 mL of toluene are stirred at reflux under dry nitrogen. Condensate from the continuous azeotropic distillation is collected in a Dean-Stark apparatus, returning the dry toluene to the reaction vessel. The water collected as a separate lower layer in the trap is greater than 90% of expected. The reaction mixture is cooled, washed with water, and the resultant organic (toluene) layer concentrated by rotary evaporation, leaving 66 g of an oily material. The reaction product is taken up in 500 g of diethylene glycol diethyl ether, and heated to 50° C. An aqueous solution of sodium bisulfite ($NaHSO_3$, 14.5 g, 0.14 mol, dissolved in 80 mL of deionized water) is added. The mixture is heated to near reflux (95° C.) with evolution of gas. After 30 h at elevated temperature, solid material (65 g, 87% crude yield) is collected by filtration. The product is the sulfosuccinate ester. $C_4F_9CH_2CH_2CH_2CH_2OOCCH_2CH(SO_3Na)COOCH_2CH_2CH_2CH_2C_4F_9$.

Example 7

$C_kF_{2kn+1}$—$(CH_2)_m$—I (100 g) where k is a blend of 6 to 16 and m =2 (7.3%), m=4 (72.54%), m=6 (18.4%) was treated with potassium acrylate (29.2 g), t-butanol (70 g), and hydroquinone (0.45 g) at 180° C. for 5 hours. The resulting product was filtered from insoluble salts and heated in vacuum to remove t-BuOH to obtain 88.8 g of $C_kF_{2k+1}$—$(CH_2)_m$—OC(O)CH=$CH_2$ acrylate wherein k is a blend of 6 to 16 and m is a blend of 2, 4 and 6. According to gas chromatography (GC) analysis the monomer obtained contained only 0.55% of the byproduct $C_kF_{(2k+1)}$—CH=$CH_2$. The acrylate was further washed with 200 mL of 10% $NaHCO_3$ aqueous solution preheated to 55° C., 200 mL of water (pH=7). The organic layer was phase separated and dissolved in 400 mL of THF. The solution was dried over $MgSO_4$, filtered, and the solvent was removed by heating in reduced pressure yielding 73.2 g (80.4%) of purified product.

What is claimed is:

1. A composition of formula I

[Rf(CH$_2$)m(O)n]x-A wherein
  $R_f$ is a straight or branched perfluoroalkyl group having from about 2 to about 20 carbon atoms, or a mixture thereof,
  m is a positive integer equal to or greater than 3,
  n is 1,
  x is 1 to 2, and
  A is —$P(O)(OR^1)_y(OM^+)_{3-y-x}$,
  $M^+$ is an alkali metal ion, $NH_4^+$, or $NH_2^+(CH_2CH_2OH)_2$,
  $R^1$ is $C_1$ to $C_3$ alkyl, and
  $R^2$ is $C_1$ to $C_4$ alkyl,
  $R^3$ is H or $CH^3$,
  y is 0 to about 1,
  d is 0 to about 16,
  e is 0 to about 16, provided that (d+e) is from about 3 to about 16.

2. The composition of claim 1 wherein n is 1, x is 1 to 2, and A is $P(O)(OR^1)_y(OM^+)_{3-y-x}$ wherein y is 0 to 1, and $M^+$ is an alkali metal ion.

3. The composition of claim 1 further comprising a surface treatment agent.

4. The composition of claim 3 wherein the surface treatment agent provides a surface effect with or without ironing which is shrinkage control, wrinkle free, permanent press, moisture control, softness, strength, anti-slip, antistatic, anti-snag, anti-pill, stain repellency, stain release, soil repellency, soil release, water repellency, oil repellency, odor control, antimicrobial, or sun protection.

5. A method of lowering the tension at the surface of contact between two phases comprising contacting said surface with a composition of Formula I

[R$_f$(CH$_2$)$_m$(O)$_n$]$_x$-A wherein
  $R_f$ is a straight or branched perfluoroalkyl group having from about 2 to about 20 carbon atoms, or a mixture thereof,
  m is a positive integer equal to or greater than 3
  n is 1,
  x is 1 to 2 , and
  A is —$P(O)(OR^1)_y(OM^+)_{3-y-x}$, $M^+$ is an alkali metal ion, $NH_4^+$, or $NH_2^+(CH_2CH_2OH)_2$,
$R^1$ is $C_1$ to $C_3$ alkyl,
$R^2$ is $C_1$ to $C_4$ alkyl,
$R^3$ is H or $CH_3$,
y is 0 to about 1,
d is 0 to about 16,
e is 0 to about 16, provided that (d+e) is from about 3 to about 16.

6. The method of claim 5 wherein the composition acts as a leveling agent.

7. The method of claim 5 wherein the phases are each independently a fibrous surface or a hard surface.

8. The method of claim 5 wherein the composition is applied as a coating to a surface.

\* \* \* \* \*